United States Patent [19]
Hasson

[11] 4,117,838
[45] Oct. 3, 1978

[54] INTRAUTERINE CONTRACEPTIVE DEVICE

[76] Inventor: Harrith M. Hasson, 345 Fullerton Pkway., Chicago, Ill. 60614

[21] Appl. No.: 777,076

[22] Filed: Mar. 14, 1977

Related U.S. Application Data

[63] Continuation-in-part of Ser. No. 719,959, Sep. 2, 1976, abandoned.

[51] Int. Cl.² ............................................. A61F 5/46
[52] U.S. Cl. .................................................. 128/130
[58] Field of Search ...................... 128/130, 127, 260

[56] References Cited

U.S. PATENT DOCUMENTS

| | | | |
|---|---|---|---|
| 3,374,788 | 3/1968 | Rosenthal | 128/130 |
| 3,516,403 | 6/1970 | Cournut | 128/130 |
| 3,842,826 | 10/1974 | Nolan | 128/130 |
| 3,881,475 | 5/1975 | Gordon et al. | 128/130 |
| 3,913,573 | 10/1975 | Gutnick | 128/130 |

*Primary Examiner*—Lawrence W. Trapp
*Attorney, Agent, or Firm*—George H. Gerstman

[57] ABSTRACT

An intrauterine contraceptive device (IUD) is provided for placement in the frontal plane of the upper uterine segment. The IUD comprises a member formed of flexible material and having a central portion, with a pair of upper arms extending outwardly and around from the central portion to form non-spiral loops in which the distal end of each of the arms does not return toward and overlap the central portion. This construction prevents the formation of a spiral under normal compression which may cause the distal ends to extend out of the main plane of the member. This construction also allows the IUD to be retained in a stable state in the frontal plane, adapts the IUD to uterine shape variations and contains a compliance property that combines transverse bend resilience with axial stiffness.

17 Claims, 21 Drawing Figures

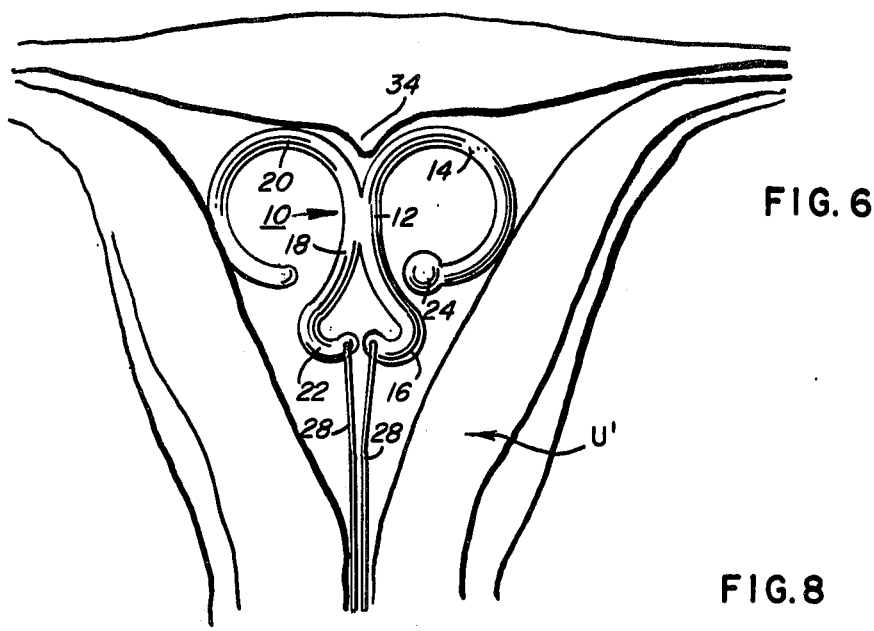
FIG. 6
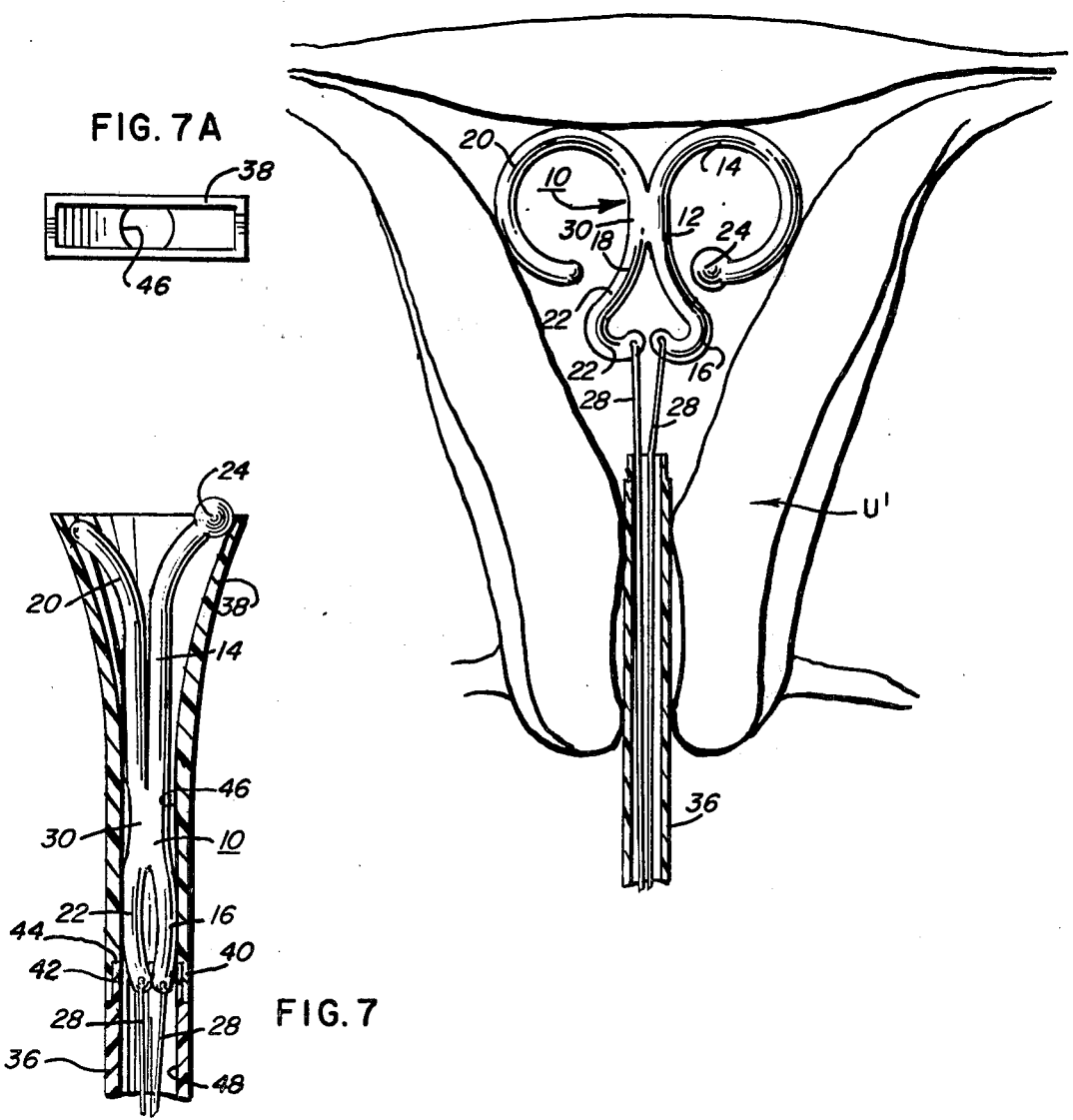
FIG. 8
FIG. 7A
FIG. 7

INTRAUTERINE CONTRACEPTIVE DEVICE

BACKGROUND OF THE INVENTION

This application is a continuation-in-part of abandoned application Ser. No. 719,959, filed Sept. 2, 1976.

This invention relates to an improved intrauterine contraceptive device (IUD).

The utility of IUD's in birth control has been established. IUD performance, however, depends on many factors, including uterine dimensions and functions. For example, a large number of uterine shape variations can exist in the presence of a uniform endometrical length. Under such circumstances, it is impossible to insert IUD's with fixed transverse diameters into endometrical cavities of unknown shapes without the occasional occurrence of a disproportion between the IUD and the cavity. Thus it is desirable that the transverse diameters of the IUD be variable in response to variations in uterine shape, in order to preserve the structural integrity of the device and the uterine cavity.

While the uterus can easily accommodate a device of reasonable size that is placed in the frontal (horizontal) plane of its endometrial cavity, it cannot tolerate a device placed in an oblique or sagittal plane of the cavity. Such misplaced devices compress the endometrium and the myometrium excessively, leading to distortion of the device and the cavity, and increase the probability of associated bleeding and pain. Therefore, consistent placement of the IUD in the horizontal plane of the endometrial cavity is a requirement of correct insertion technique.

It is important that the IUD be placed entirely above the uterine isthmus. Proper IUD positioning requires prior knowledge of cervical length, as well as endometrial length. Knowing the length of the cervix permits one to insert the IUD consistently above the level of the internal cervical OS, and awareness of the endometrial length allows one to place the device in the upper uterine segment. It has been found that the best performance was obtained when the length of the IUD was shorter than the length of the endometrical cavity by 1.25 to 1.75 cm. Placement of an IUD entirely in the more spacious upper uterine segment can be accomplished if the length of the IUD is approximately 1.0 to 1.75 cm shorter than the length of the cavity.

In order to increase the likelihood of the IUD being retained in the uterine cavity, it is preferable that the IUD be of suitable size and placed in the upper uterine segment. The IUD should also be provided with mechanical means capable of resisting the effects of uterine contractions that tend to move it downwards in the direction of the cervix. Downward gravitation of an IUD is resisted at the level where the transverse diameter of the IUD is greater than the transverse diameter of the uterine cavity. The level at which the surface resistance occurs depends on the relative width of the IUD and that of the cavity. Devices with fixed transverse diameters are suspended in the upper uterine segment, if the area of IUD-uterine contact is near the fundus. However, such devices may come to rest at a lower position in the cavity, if the transverse diameter of the fundus is broader than that of the IUD.

It is, therefore, an object of the present invention to provide an IUD that can be relatively easily and simply placed entirely above the uterine isthmus.

Another object of the present invention is to provide an IUD having a transverse diameter that is not fixed, but is instead variable in response to variations in uterine shape.

A further object of the present invention is to provide an IUD that is capable of resisting the effects of uterine contractions that tend to move it downwards in the direction of the cervix.

IUD retention may be due to suspension of its upper portion in the fundus and/or abutment of its lowermost portion against the uterine walls. The dynamic cyclic changes that occur in the fundal and isthmus uterine segments create optimal conditions for IUD expulsion during menstruation. It is, therefore, an object of the present invention to provide an IUD having a shape in which the lower portion thereof may abut the uterine wall to maintain the IUD in substantially its initial high position of placement.

A type of IUD that is constructed to prevent expulsion is disclosed in Hasson U.S. Pat. No. 3,467,089 and Nolan U.S. Pat. No. 3,842,826. While the IUDs disclosed in those patents have increased retention capability and thus are not easily expelled, the IUDs are relatively difficult to remove because the lower wings must be large to provide good retention. Further, when the IUDs of those patents are implanted in the uterus, the lower wings are spread out causing good retention, but expulsive forces will bend these wings upwardly making their transverse dimensions smaller. In fact, to remove the IUDs of those patents, the IUD is pulled downwardly thereby forcing the lower wings to bend upwardly and permitting the IUD to be removed.

It is an object of the present invention to provide an IUD that has good retention capability and thus is not easily expelled, but is relatively simple to remove. To this end, the present invention provides an IUD that includes a lower portion which tends to open, providing a greater transverse diameter, when the uterus contracts and pushes the IUD downwardly. Thus as the uterus contracts, the IUD of the present invention tends increasingly to resist expulsion. Additionally, means are provided for removing the IUD of the present invention in a relatively simple manner, by using a pulling force that tends to straighten out the lower portion.

Another problem with the IUDs disclosed in U.S. Pat. No. 3,467,089 is that this prior art IUD is shown being constructed with elongated inner wires which serve to form the cores of the wings, extending from an elongated stem. The possibility exists that one of the inner wires may become dislodged from its inside position, causing it to extend through the surrounding resilient material. This has the potential of resulting in perforation of the uterus, and it is therefore desirable to avoid the necessity for using any wire which could penetrated plastic in the IUD.

It is, therefore, an object of the invention to provide an IUD which does not require inner wires in its construction. Cervical perforations have been reported with the use of stemmed devices, such as the copper T, copper 7 or Saf-t-Coil. The mechanism of perforation is related to the method of retention of the IUD. Stemmed devices take an oblique position in the uterine cavity either through faulty insertion or subsequent movement of the IUD caused by uterine contractions. Under such circumstances, the IUD is retained in the uterus by anchoring of the lower tip of its stem into the uterine wall at the level of the isthmus or cervix. Continued myometrial pressure causes the tip to penetrate the uterine wall partially or completely.

Therefore, another object of the present invention is to provide an IUD that is constructed without an extending stem or tip, in order to prevent penetration of the uterine wall by such stem or tip.

A relationship has been found between IUD compliance (resiliency) and the undesirable expulsion of the IUD from the uterus. It has been found that there is less undesirable expulsion when the IUD has a significant degree of transverse bend resilience. It is, therefore, an object of the present invention to provide an IUD having relatively high longitudinal stiffness and relatively high transverse bend pliability.

A type of prior art IUD which employs a pair of oppositely extending loops is disclosed in Rosenthal U.S. Pat. No. 3,374,788. In this Rosenthal patent, the loops are coiled to form a generally spiral configuration. In the Rosenthal patent, such coiling occurs in the molded state prior to insertion in the uterus. This has been found to be disadvantageous, in that if the loop are initially coiled, then they cannot coil further to any significant degree when placed in a restrictive space. Thus if Rosenthal's IUD is placed in a relatively small uterine space (in which the transverse diameter of the uterus is smaller than that of the IUD), the loops may bend anteriorly or posteriorly in the most accessible plane, thereby causing IUD distortion and undue distention of the limited uterine depth space. Knotting, distortion and overlapping upon removal may occur.

It is, therefore, an object of the present invention to provide an IUD in which the loops are not coiled in the molded state, but are instead structured with a memory for coiling. In this manner, when the loops are placed in a space with a smaller transverse diameter than that of the loops, they will coil inward without bending. This shape provides a safety factor against IUD distortion and related symptomatology.

Other objects and advantages of the present invention will become apparent as the description proceeds.

BRIEF DESCRIPTION OF THE INVENTION

In accordance with the present invention, there is provided an IUD which includes a double loop configuration in its upper section in order to utilize space created by fundal anomalies and to adapt to the compressive and distortive stress of urterine contractions. The IUD additionally includes a middle section with sufficient stiffness to resist distortion and a lower section with a diameter enlarged sufficiently to resist downward displacement.

In the illustrative embodiment, the IUD includes a member adapted for insertion in the uterus formed of flexible material and having a central portion. A first upper arm extends outwardly and around from the central portion to form a non-spiral loop in which the distal end of the arm does not return toward and overlap the central portion. A lower arm extends downwardly from the central portion, then outwardly and inwardly to form a retaining member. Another upper arm extends outwardly and around from the central portion in a direction opposite from the first arm to form another non-spiral loop in which the distal end of the other arm does not return toward and overlap the central portion. In this manner, under normal compression the distal ends will remain in the main plane of the member.

In one embodiment, the lower arm has a filament connected thereto and defines a recessed portion acting as a hinge. The lower arm is sufficiently flexible so as to allow easy straightening of the lower arm when the filament is pulled downwardly.

A more detailed explanation of the invention is provided in the following description and claims, and is illustrated in the accompanying drawings.

BRIEF DESCRIPTION OF THE DRAWINGS

FIG. 6 is a view of an IUD constructed in accordance with the principles of the present invention, implanted in a uterus with a fundal abnormality;

FIG. 7 is a fragmentary cross-sectional view of an instrument designed for implanting the IUD in a uterus, with the IUD shown in full;

FIG. 7A is a top view thereof without the IUD being shown;

FIG. 8 is a view showing a typical means for introducing into the uterus an IUD constructed in accordance with the principles of the present invention;

DETAILED DESCRIPTION OF THE ILLUSTRATIVE EMBODIMENT

Figure 1:
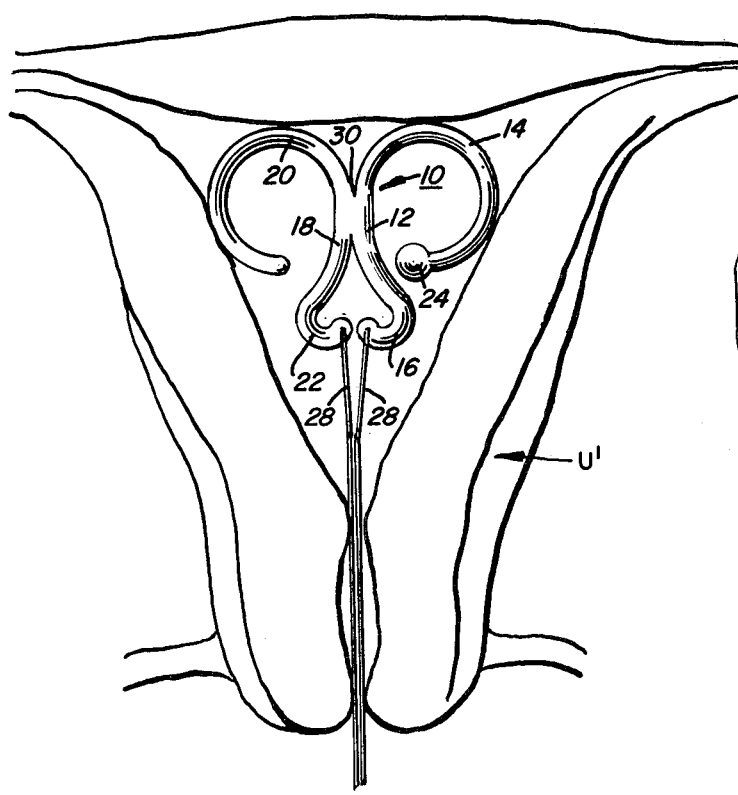
FIG. 1 is a view of an IUD constructed in accordance with the principles of the present invention, implanted in a uterus.

Referring to FIGS. 1-8 of the drawings, an intrauterine device (IUD) 10 is shown therein, and is shaped and preformed to provide a first resilient member 12 having a first upper loop portion 14 and a second lower loop portion 16, which loop portions are contiguous and form a generally S-shaped configuration. IUD 10 also comprises a second member 18 having a third upper loop portion 20 and a fourth lower loop portion 22, which loop portions are contiguous and form a generally S-shaped configuration. The generally S-shaped members 12 and 18 are connected in back-to-back relationship, by molding, for example, so that one viewing IUD 10 sees an S-shaped configuration on one side and a reverse S-shaped configuration on the other side.

Upper loop portions 14 and 20 are considerably larger than lower loop portions 16 and 22. The upper loop portions each essentially comprise an arm which extends outwardly and around to form the loop while the lower loop portions 16 and 22 each essentially comprise an arm extending outwardly and around in a direction opposite from the upper loop portion arms to form the loop.

The specific shape of the upper loop portions 14 and 20 accommodate unknown variations in uterine shape and provide a fundal seeking property. The trunk which interconnects the loop portions is short and stiff to resist distortion and the lower loop portions are enlarged sufficiently to resist downward gravitation and expulsion.

Although member 12 is similar in size and configuration to member 18, the arm forming loop 14 is slightly longer than the arm forming loop 20 and has a rounded end or bead 24 at its distal end. In this manner, when IUD 10 is inserted into the uterus, bead 24 is the first item out of the tube which directs the IUD into the uterus, and bead 24 acts to lead the way into the uterus.

As shown in the drawings, the upper loop portions 14 and 20 are not initially coiled. Bead 24 is separate from the beginning portion of loop 14 in the molded preinsertion state and loop 14 is considered to be a non-spiral. In this manner, when loop portions 14 and 20 are placed in a space with a smaller transverse diameter than that of the loop portions, they will coil inward without bending anteriorly or posteriorly.

Lower loops 16 and 22 each define an opening 26 through which a filament or string 28 is connected for use in removing the IUD from the uterus.

Referring now in particular to FIG. 1, an IUD 10 is shown therein implanted in the frontal plane of the endometrial cavity of uterus U', above the uterine isthmus. It can be seen that IUD 10 is conveniently supported within the endometrial cavity by circumferential portions of upper loops 14 and 20. It can also be seen that if the endometrial cavity were narrower in transverse dimension, the IUD would remain conveniently placed therein because upper loops 14 and 20 would tend to become closed, or smaller, in response to the smaller dimension of the uterus. Likewise, if the endometrial cavity were wider in transverse dimension, the IUD 10 would remain conveniently placed because upper loops 14 and 20 would open in response to the wider dimension.

It can also be seen that if an expulsive force would move IUD 10 downwardly so that lower coils 16 and 22 would be urged against the uterine wall, as the expulsive force increases downwardly the transverse diameter of lower loops would actually increase thereby providing greater resistance to expulsion.

It is preferred that the IUD 10 be molded of conventional IUD material. As a specific example, although no limitation is intended, the IUD could be molded of a composition comprising approximately 80 percent ethylene vinyl acetate (EVA), 10 percent polyester and 10 percent resin, or the IUD could be molded of a composition comprising approximately 80 percent EVA with the remainder polyester and resin in suitable proportions as is well-known in the art.

Members 12 and 18 could be molded separately and then fastened together to form the unit shown in the drawings. Alternatively, the entire IUD 10 could be molded as a unitary member, except for filaments 28 which would be attached subsequently.

Figure 4:
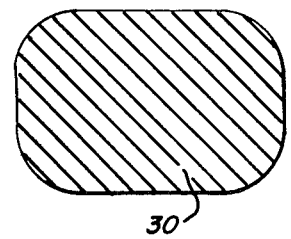
FIG. 4 is a cross-sectional view thereof, taken along the plane of the line 4—4 of FIG. 2.
Figure 5:
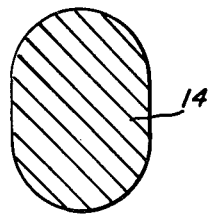
FIG. 5 is a cross-sectional view thereof, taken along the plane of the line 5—5 of FIG. 2.
Figure 3B:
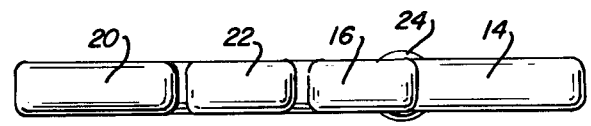
FIG. 3B is a bottom view thereof, taken along the plane of the line 3B—3B of FIG. 2.
Figures 2, 3A:
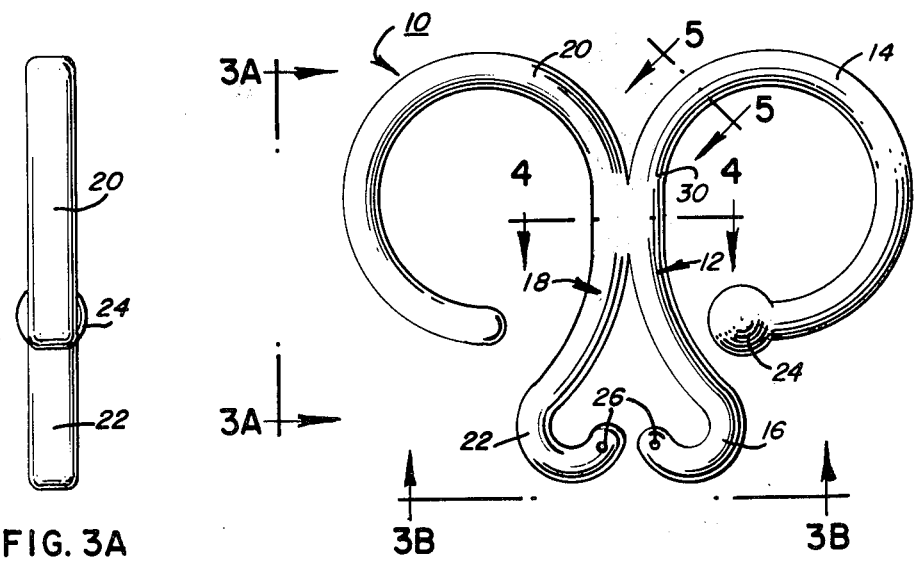
FIG. 2 is a front view of an IUD constructed in accordance with the principles of the present invention.
FIG. 3A is a side view thereof, taken along the plane of the line 3A—3A of FIG. 2.

In this manner, IUD 10 has resilient arms 14, 20, 16 and 22 to provide a transverse bend resilience but also has a doubled or a thick section 30 which, as a result of its dimensions, is relatively stiff to give the IUD 10 proper axial stiffness. As shown in FIGS. 4 and 5 in particular, the cross-sectional configuration of the arms and section 30 are preferably non-circular and may be generally elliptical.

The IUD 10 can carry anti-fertility material. There are numerous ways in which such anti-fertility material could be connected to IUD 10, but it is preferred that such anti-fertility material be carried by upper loops 14 and 20, as well as thick section 30, on the theory that the anti-fertility material is most effective when it is at a high position within the endometrial cavity. In some circumstances, the anti-fertility material may be a copper wire; in other instances it may be a coating of copper or zinc on the IUD 10. Other conventional anti-fertility materials may be used, if desired, such as hormonal agents, e.g., progesterone. The hormonal or chemical agent may be carried by the IUD 10 in the form of a sleeve or other suitable forms. In another construction, the anti-fertility material may be molded into the substance of the IUD.

Because of the unique construction of IUD 10, there is no need for using inner wire, such as used in the IUD disclosed in U.S. Pat. No. 3,467,089. Thus the potential of wire penetration is obviated by the present invention.

FIG. 6 illustrates a uterus U' having a congenital fundal abnormality 34. Although it is desirable for the IUD to be high in the endometrial cavity, certain prior art IUD's are prevented from being located in the upper segment as a result of this fundal abnormality. It can be seen with reference to FIG. 6 in particular, however, that the fundal abnormality is accommodated by IUD 10, which IUD is present in the fundus notwithstanding the anatomic abnormality.

The method of inserting IUD 10 is illustrated in FIGS. 7, 7A and 8. An insertion tube 36 has a funnel 38 connected to one end thereof. Funnel 38 has a lower rim 40 which fits into an annular recessed portion 42 defined at the top 44 of insertion tube 36. The internal diameter 46 at the lower portion of funnel 38 is equal to the internal diameter 48 of tube 36. In this manner, a smooth, unobstructed internal wall is provided when the funnel 38 is connected to the insertion tube 36.

The IUD 10 to be inserted in the uterus is first inserted into tube 36 by introducing filaments 28 through funnel 38 and tube 36 and then pulling filaments 28 downwardly. Such downward forces on filaments 28 will extend and straighten lower loops 16 and 22 in the manner illustrated in FIG. 7 and IUD 10 can be pulled downwardly into tube 36 until upper loops 14 and 20 have substantially passed through funnel 38 and bead 24 is the only portion remaining outside of tube 36. Funnel 38 is then removed or disengaged from tube 36. Thereafter, tube 36 is introduced into the uterus U as illustrated in FIG. 8. A rod (not shown) is used to stabilize IUD 10 and to push it slightly forward into the frontal plate of the endometrial cavity. Tube 36 is then pulled downwardly over the remainder of IUD 10 and the IUD becomes implanted in the endometrial cavity as a coiled unit, using a withdrawal method of IUD insertion. A tenaculum is applied on the cervix to stabilize the uterus, straighten the angle between the body and neck of the uterus and to provide a counter force, when traction is applied to it, to enhance the ease and safety of the insertion.

When IUD 10 is to be removed from the uterus, filaments 28 are pulled downward to thereby extend or straighten arms 16 and 22 downwardly in the manner illustrated in FIG. 7 to thereby allow the IUD to be removed in a relatively simple, efficient manner.

It is preferred that the vertical length of the IUD 10 be less than the overall width of the IUD. Additionally, it is preferred that the maximum transverse dimension of lower loop portions 16, 22 be less than 50 percent of the maximum transverse dimension of upper loop portions 14, 20. These proportions are useful in adapting the IUD 10 to fit the shape of the uterine cavity and particularly the shape of the upper uterine segment.

Various modifications of the IUD 10 of the present invention are shown in FIGS. 9–19. In FIGS. 9–19, the same reference numerals are used to represent similar structure.

Figure 9:
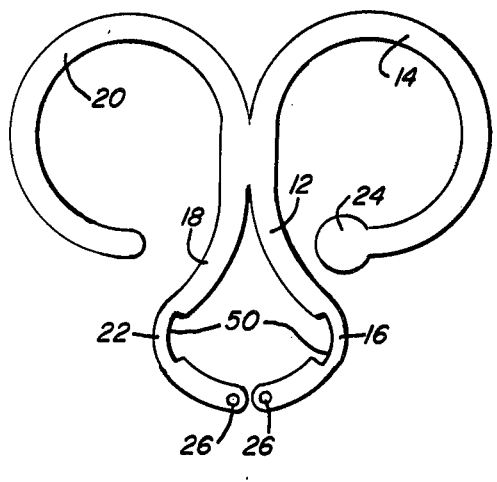
FIG. 9 is a front view of an IUD constructed in accordance with a second embodiment of the present invention.

In the IUD of FIG. 9, upper loops 14, 20 are identical to upper loops 14, 20 of the FIGS. 1–8 embodiment, but lower loops 16, 22 have been modified so as to extend toward each other without curling upwardly. Additionally, recessed portions 50 are defined by the lower loops to form hinges, thereby providing greater flexibility when the filaments coupled to openings 26 are pulled. This hinge effect on the lower loops 16, 22 increases the ease of loading the IUD into inserter tube 36. The hinge effect also increases the ease of IUD removal from the uterus and establishes a significant difference between the force required to expel the IUD from the uterus and that required to remove it by pulling the filaments.

As stated previously, downward pressure of the IUD against the uterine wall tends to increase the diameter of the lower loops and thus resist expulsion. In contrast, pulling on the filaments easily straightens the lower loops and allows simple removal.

Figure 10:
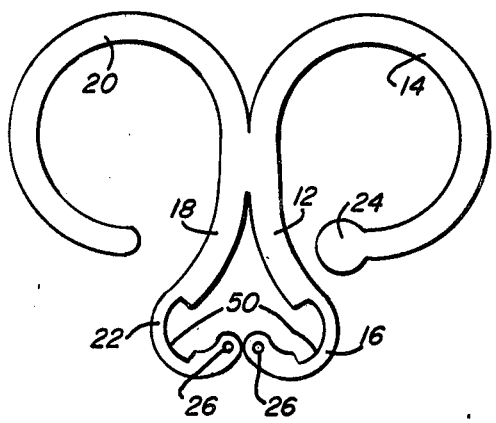
FIG. 10 is a front view of an IUD constructed in accordance with a third embodiment of the present invention.

The FIG. 10 embodiment is similar to the FIGS. 1–8 embodiment of the invention, but in the embodiment of FIG. 10, recesses 50 are defined by lower loop portions 16, 22, to provide a hinging action as discussed above.

Figure 11:
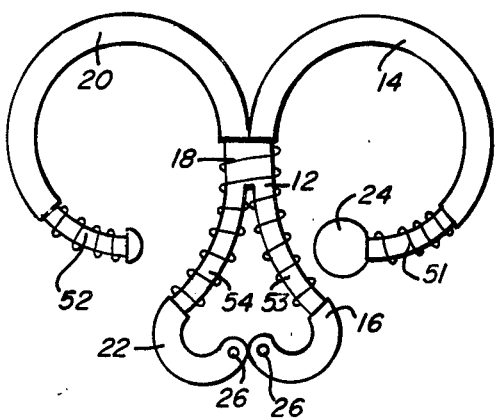
FIG. 11 is a front view of an IUD constructed in accordance with a fourth embodiment of the present invention.

In the embodiment of FIG. 11, portions 51, 52, 53 and 54 have a smaller cross-sectional area than the remaining portions of the IUD. In this manner, the IUD may carry an anti-fertility agent in the form of a coil which is wound around portions 51–54, with the cross-sectional diameter of the IUD being unchanged as a result of the additional coil. In other words, the coil which is wound about the portions 51–54 of the IUD will not increase the cross-sectional diameter of the IUD to any extent greater than the diameter of the other portions of the IUD.

Figure 12:
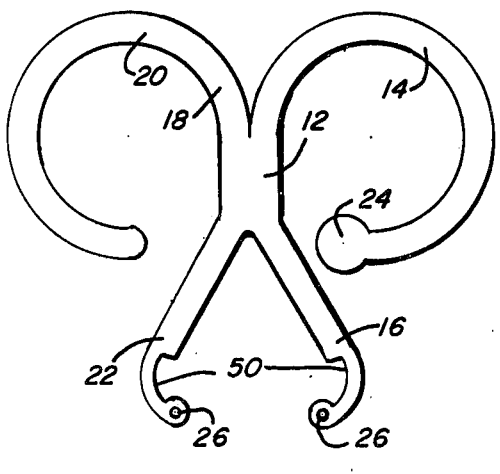
FIG. 12 is a front view of an IUD constructed in accordance with a fifth embodiment of the present invention.

In the embodiment of FIG. 12, the distal ends of lower loop portions 16, 22 are spaced further apart than in other embodiments. Additionally, recesses 50 are defined by the lower loop portions to provide the hinge effect described above.

Figure 13:
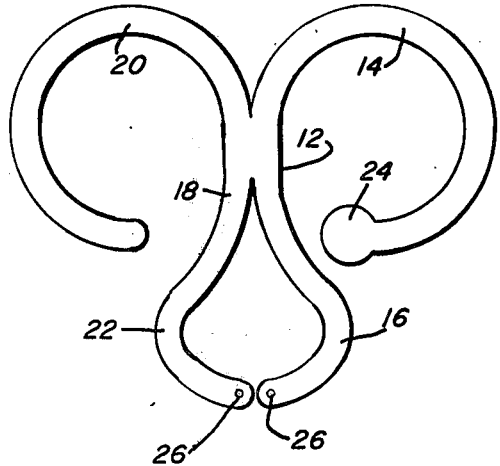
FIG. 13 is a front view of an IUD constructed in accordance with a sixth embodiment of the present invention.

The embodiment of FIG. 13 is constructed similarly to the embodiment of FIG. 9; however, recesses 50 of the FIG. 9 embodiment are not defined by the lower loop portions 16, 22 of the FIG. 13 embodiment.

Figure 14:
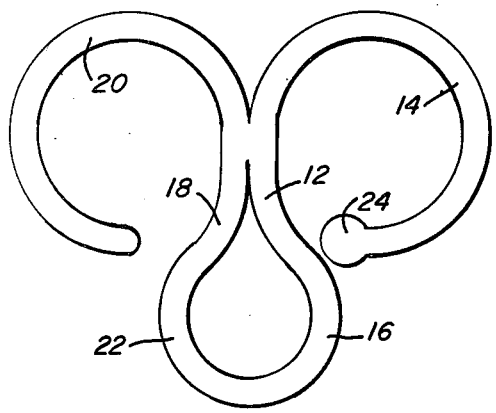
FIG. 14 is a front view of an IUD constructed in accordance with a seventh embodiment of the present invention.
Figure 15:
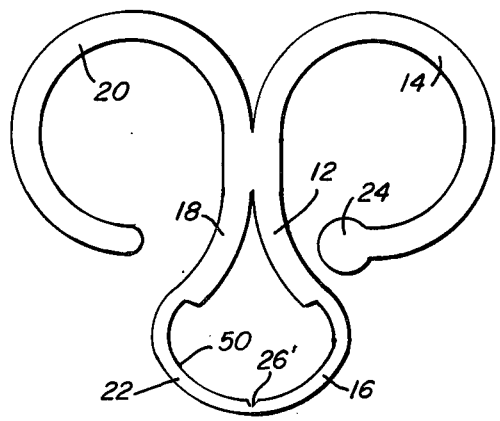
FIG. 15 is a front view of an IUD constructed in accordance with an eighth embodiment of the present invention.
Figure 16:
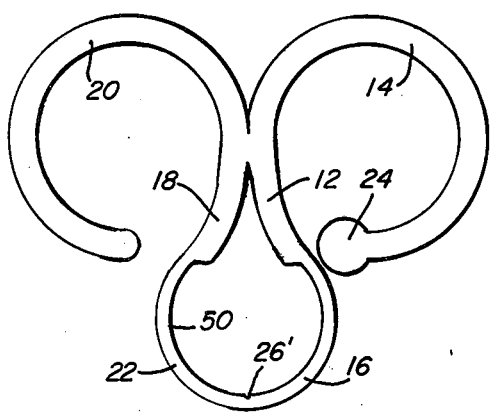
FIG. 16 is a front view of an IUD constructed in accordance with a ninth embodiment of the present invention.

In the embodiments of FIGS. 14–16, the loop portions 16, 22 forming the lower retaining member are integrally connected to each other to form a continuous single loop below upper loops 14, 20. In the embodiments of FIGS. 15 and 16, a recess 50 is defined by the lower loop to provide a hinge effect as described above. Further, a groove 26' is provided for coupling to a filament, in a similar manner to openings 26 which are defined by the lower loop portions in other embodiments.

Figure 17:
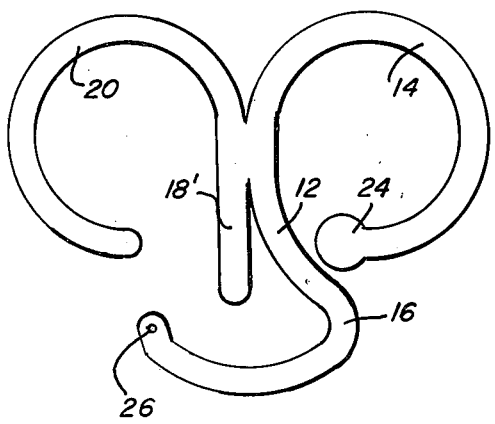
FIG. 17 is a front view of an IUD constructed in accordance with a tenth embodiment of the present invention.
Figure 18:
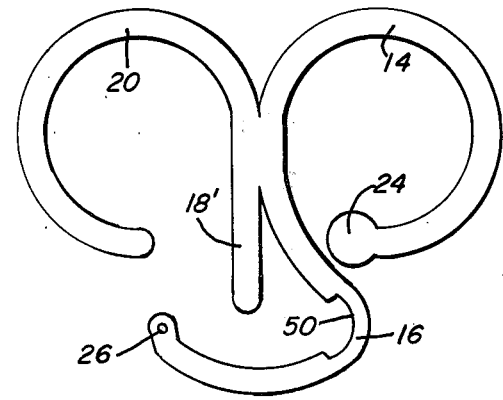
FIG. 18 is a front view of an IUD constructed in accordance with an eleventh embodiment of the present invention.

In the FIGS. 17–18 embodiments, member 18' is discontinued and second lower loop portion 16 is used as the retaining member. In the FIG. 18 embodiment, member 16 defines a recess 50 to provide a hinge effect and in both the FIGS. 17 and 18 embodiment, opening 26 is defined adjacent the distal end of portion 16 for coupling a filament thereto. The operation of the IUD of FIGS. 17 and 18 is similar to the operation of the IUD of the other embodiments.

Figure 19:
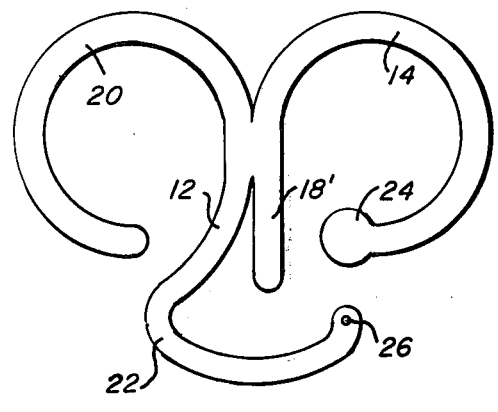
FIG. 19 is a front view of an IUD constructed in accordance with a twelfth embodiment of the present invention.

The FIG. 19 IUD is similar to the FIGS. 17 and 18 embodiments, but in the FIG. 19 embodiment lower portion 22 is the retaining member while member 12' is discontinued. Lower member 22 defines an opening 26 adjacent its distal end for coupling to a filament, to be operated in the manner described above in connection with the other embodiments.

It can be seen that the IUDs of the present invention can be easily loaded into an inserter tube by pulling downwardly on the filament or filaments. The hinging effect in specific designs aids in tending to straighten the lower members. The shape of the funnel member 38 of the inserter (FIG. 7) forces the lower loop portions to straighten and lead them into the inserter 38 without difficulty. After the IUD is loaded into the inserter, the funnel is disconnected and the insertion is then performed.

Although illustrative embodiments of the invention have been shown and described, it is to be understood that various modifications and substitutions may be made by those skilled in the art without departing from the novel spirit and scope of the invention.

What is claimed is:

1. An intrauterine contraceptive device which comprises: a member adapted for insertion in the uterus formed of flexible material and having a central portion; a first upper arm extending outwardly and around from said central portion and back toward said central portion to form a first loop; a second arm extending downwardly from said central portion, then outwardly and inwardly to form a retaining member; and a third upper arm extending outwardly and around from said central portion and back toward said central portion in a direction opposite from said first arm to form another loop, the distal ends of said first and third upper arms being substantially non-overlapping with respect to said central portion to prevent the formation of a spiral under normal compression which may cause said distal ends to extend out of the main plane of the member, said second arm defining a hinge portion; a filament connected to said second arm, said hinge and filament cooperating to permit said second arm to be straightened easily when the filament is pulled downwardly.

2. An intrauterine contraceptive device as described in claim 1, in which said member is formed of solid material and said central portion is rigid so as to have sufficient stiffness to resist distortion in the uterus, said central portion having a substantially equal length and width.

3. An intrauterine contraceptive device as described in claim 1, and further including a fourth arm portion extending downwardly from said central portion, then outwardly and inwardly toward said second arm portion.

4. An intrauterine contraceptive device as described in claim 3, in which said second and fourth arm portions are connected to form a continuous loop.

5. An intrauterine contraceptive device as described in claim 4, in which said member comprises the integral formation of said first, second, third and fourth arms and said central portion.

6. An intrauterine contraceptive device as described in claim 1, in which said member defines recessed portions for receiving anti-fertility material.

7. An intrauterine contraceptive device as described in claim 6, in which said anti-fertility material comprises a metallic coil wound about said recessed portions, with the cross-sectional area of the coil wound about said recessed portions being no greater than the cross-sectional area of the non-recessed portions of said member.

8. An intrauterine contraceptive device as described in claim 1, which is molded of a composition comprising approximately 80 percent ethylene vinyl acetate, 10 percent polyester and 10 polyester resin.

9. An intrauterine contaceptive device which comprises: a member adapted for insertion in the uterus formed of flexible material and having a central portion; a first upper arm extending outwardly and around from said central portion and back toward said central portion to form a non-spiral loop in which the distal end of said arm does not overlap said central portion; another upper arm extending outwardly and around from said central portion and back toward said central portion in a direction opposite from said first arm to form another non-spiral loop in which the distal end of said other arm does not overlap said central portion, whereby under normal compression said distal ends will remain in the main plane of the member; a lower retaining member having a filament connected thereto, said lower retaining member defining a hinge portion and thus being sufficiently flexible so as to allow easy straightening of said lower retaining member when said filament is pulled downwardly, said lower retaining member comprising a pair of loop portions that are adjacent to each other and extend away from the central portion and then toward each other.

10. An intrauterine contraceptive device as described in claim 9, in which said loop portions forming said lower retaining member are integrally connected to each other to form a continuous single loop below said two upper loops.

11. An intrauterine contraceptive device as described in claim 9, said lower retaining member having a transverse dimension that is less than fifty percent of the transverse dimension of both upper arms.

12. A device as described in claim 1, wherein said hinge portion comprises a recessed portion defined by said second arm.

13. A device as described in claim 3, said fourth arm defining a hinge portion; a filament connected to said fourth arm, said hinge and said filament cooperating to permit said fourth arm to be straightened easily when the filament is pulled downwardly.

14. A device as described in claim 13, wherein said hinge portion comprises a recessed portion defined by said fourth arm.

15. A device as described in claim 1, said first upper arm and said third upper arm each extending around approximately three-fourths of a circle in their uncompressed position.

16. A device as described in claim 9, said upper arms each extending around approximately three-fourths of a circle in their uncompressed position.

17. A device as described in claim 9, wherein said hinge portion comprises a recessed portion defined by said lower retaining member.

* * * * *